United States Patent
van Wijck

(10) Patent No.: US 6,258,950 B1
(45) Date of Patent: Jul. 10, 2001

(54) METHOD FOR THE PREPARATION OF MELAMINE

(75) Inventor: Julius G. T. van Wijck, Maastricht (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/239,149

(22) Filed: Jan. 28, 1999

Related U.S. Application Data

(63) Continuation of application No. PCT/NL97/00431, filed on Jul. 21, 1997.

(30) Foreign Application Priority Data

Jul. 30, 1996 (NL) .................................................. 1003709

(51) Int. Cl.$^7$ ...................... C07D 251/60; C07D 251/62
(52) U.S. Cl. ........................... 544/200; 544/201; 544/198
(58) Field of Search ..................................... 544/200, 201

(56) References Cited

U.S. PATENT DOCUMENTS

| | | | |
|---|---|---|---|
| 3,116,294 | 12/1963 | Marullo et al. | 544/201 |
| 4,565,867 | 1/1986 | Thomas et al. | 544/201 |
| 5,514,796 | 5/1996 | Best et al. | 544/201 |
| 5,514,797 | 5/1996 | Best et al. | 544/201 |
| 5,721,363 | * 2/1998 | Canzi et al. | 544/201 |

FOREIGN PATENT DOCUMENTS

| | | |
|---|---|---|
| 0 747 366 | 12/1996 | (EP) . |
| 96/20182 | 7/1996 | (WO) . |
| 96/20183 | 7/1996 | (WO) . |
| 96/23778 | 8/1996 | (WO) . |

* cited by examiner

Primary Examiner—John M. Ford
Assistant Examiner—Venkataraman Balasubramanian
(74) Attorney, Agent, or Firm—Pillsbury Winthrop LLP

(57) ABSTRACT

The invention relates to a high-pressure process for producing melamine from urea in which highly pure melamine is obtained by transferring melamine melt leaving a melamine reactor to a cooling vessel where the melamine melt is cooled to a temperature of between 1° C. and 30° C. above the melting point of melamine after which the liquid melamine can be transferred to a second cooling vessel in which vessel the melamine melt is further cooled using cold ammonia by which solid melamine is obtained.

15 Claims, No Drawings

METHOD FOR THE PREPARATION OF MELAMINE

This application is a continuation of PCT/NL97/00431, filed Jul. 21, 1997.

FIELD OF THE INVENTION

The invention relates to a method for the preparation of solid melamine using a high-pressure process in which the melamine melt is transferred from the reactor to a vessel and is cooled using ammonia as to obtain melamine having a very high degree of purity (98.5 wt. % to 99.95 wt. %) as a dry powder directly from the reactor product.

DESCRIPTION OF THE PRIOR ART

Melamine (2,4,6-triaminosymtriazine) is a white crystalline product obtained by heating urea.

Purified crystalline melamine can be combined with formaldehyde to form melamine resin. Characteristics of subsequent products formed from the melamine resin are critically dependent upon the level of purity of the crystalline melamine used to form the resin. Obtaining crystalline melamine of very high purity is therefore an essential first step to melamine related product formulation.

The first step in melamine resin formation from crystalline melamine is the production of trimethylol melamine. This molecule can combine further with others of the same kind by a condensation reaction. Excess formaldehyde or melamine can also react with trimethyol melamine or its polymers, providing many possibilities of chain growth and cross-linking. The nature and degree of polymerization can be varied by pH and the degree of heat applied in the curing process. Impurities in the melamine also effect the nature of the polymerization reaction.

A major advantage of melamine resins is that they are more water resistant and heat resistant than urea resins. Melamine resins may be water-soluble syrups (low molecular weight) or insoluble powders (high molecular weight) dispersible in water. Melamine resins are widely used as molding compounds with α-cellulose, wood flour, or mineral powders as fillers and with coloring materials. Melamine resins are also used in laminating, producing boil-proof adhesives, increasing the wet strength of paper, textile treatment, leather processing, and producing dinnerware and decorative plastic items. The use of melamine resins in general results in superior products over urea resin products.

Butylated melamine resins are formed by incorporating butyl or other alcohols during resin formation. These resins are soluble in paint and enamel solvents and in other surface coatings, often in combination with alkyds. They give exceptional curing speed, hardness, wear resistance, and resistance to solvents, soaps and foods.

Melamine-acrylic resins are water soluble and are used for formation of water-base industrial and automotive finishes. The use of melamine-acrylic resins provides smooth, durable surface finishes. However, as is the case with other melamine-based products, the superiority of melamine-acrylic resin products is related to the high level of purity of the initial crystalline melamine product.

A high level of purity is in particular required when melamine is used for the production of resins for coatings. Transparency and colourless are properties which are required for these applications.

A method of obtaining melamine crystals is described in U.S. Pat. No. 4,565,867 issued to Thomas et al., the complete disclosure of which is incorporated herein by reference. The Thomas reference discloses a high-pressure process for the preparation of melamine from urea. In particular, the pyrolysis of urea in a reactor at a pressure of about 10.3 MPa to about 17.8 MPa and a temperature of about 354° C. to about 427° C. for producing a reactor product is described.

This reactor product contains liquid melamine, $CO_2$ and $NH_3$ and is transferred under pressure, as a mixed stream, to a separator. In this separator, which is kept at virtually the same pressure and temperature as the reactor, the reactor product is separated into a gaseous stream and a liquid stream. The gaseous stream contains $CO_2$ and $NH_3$ off-gases and also melamine vapour. The liquid stream substantially consists of liquid melamine. The gaseous stream product and the liquid stream product are treated differently. The gaseous product is transferred to a scrubber unit, while the liquid melamine is transferred to a product cooler. In the scrubber unit the above-mentioned $CO_2$ and $NH_3$ off-gases, which contain melamine vapour, are scrubbed, at virtually the same pressure as the reactor pressure, with molten urea so as to pre-heat the urea and cool said off-gases and remove the melamine that is present from the off-gases. The pre-heated molten urea, which contains melamine, is then fed to the reactor. In the product cooler the liquid melamine is reduced in pressure and cooled by means of a liquid cooling medium (preferably liquid ammonia) so as to produce a solid melamine product without washing or further purification.

The disadvantage of the above-mentioned Thomas method is that melamine having a purity which is insufficient for a number of critical applications, like resins for coatings. Thomas teaches a theoretical conversion yielding only 99.19 wt. % pure melamine. However, the example provided by the Thomas reference at column 9, line 61 through column 10, line 2, shows the Thomas method obtaining melamine with an even lower purity of only 98.0 wt. %. In the Thomas example, the melamine product remains 0.81 wt. % urea, 0.03 wt. % $CO_2$, 0.05 wt. % melamine-related compounds and 0.07 wt. % organic solids (melem, melam, and other solids). However if the Thomas method is used in practice, the maximum purity is only 97.5 wt. %, measured by High Performance Liquid Chromatography (HPLC). Such a product is not pure enough for universal application.

A need therefore exists to provide an economical method to obtain highly pure melamine (98.5 wt. % to 99.95 wt. % and preferably 99.5 wt. % to 99.95 wt. %).

SUMMARY OF THE INVENTION

An object of the present invention is to obtain an improved high-pressure process for the preparation of melamine from urea in which melamine having a high degree of purity is obtained as a dry powder directly from the reactor product. More particularly it is an object of the present invention to obtain an improved high-pressure process for the preparation of melamine from urea in which melamine having a high degree of purity is obtained as a dry powder directly from the liquid melamine melt through cooling using ammonia.

The present invention provides a method of preparing highly pure solid melamine from urea melt obtained from a urea plant, the method comprising the combination of steps of:

(a) providing urea melt to a scrubber unit to effect separation of a liquid phase from a gas phase producing a urea melt mixture;

(b) transferring the urea melt mixture from the scrubber unit to a melamine reactor and heating the urea melt mixture to produce a melamine melt and off-gases; and (c1) separating said off-gases from said elamine melt and (c2) transferring the melamine melt to a first cooling vessel, the pressure in the cooling vessel being at a certain pressure preferably higher than 5 MPa and cooling the melamine melt to a temperature just above the melting point of melamine, preferably to between 1° C. to 30° C. and more preferably- to between 1° C. to 10° C. above the melting point of melamine.

(d) transferring the melamine melt to a second cooling vessel in order to convert the liquid melamine to a solid product, wherein in the second cooling vessel the melamine is further cooled using cold ammonia, preferably liquid ammonia to produce a solid pure melamine product.

Cold ammonia means ammonia with a temperature below the temperature of the melamine melt and is generally between 20 to 380° C., preferably between 50 to 300° C. to produce a solid pure melamine product.

During the further cooling in the second cooling vessel using ammonia, the melamine melt is cooled at least 10° C., preferably at least 50° C. and more preferably at least 100° C. Additional cooling may be obtained by expanding partly or as a whole the mixture of melamine melt and ammonia.

Optionally, the melamine melt in the process of conversion to a solid product can be expanded by lowering the pressure in the second cooling vessel to produce a solid pure melamine product.

The present invention provides an alternative method of preparation of highly purified solid melamine from urea melt obtained from a urea plant, the method comprising as step (c2):

(c2) transferring the melamine melt to a first cooling vessel and cooling the melamine melt and gradually raising the pressure in the vessel through for example the introduction of ammonia; and (d) thereafter, the liquid melamine is, prior to conversion to solid melamine, transferred to a second cooling vessel and further cooled through the introduction of cold ammonia and expanded to produce highly pure solid melamine.

Preferably the cooling in the first vessel of the melamine melt is done by gradually raising the pressure in the vessel with at least 2 MPa. Preferably the pressure in the vessel is raised to a level above 10 MPa, more preferably above 20 MPa, more in particular above 50 MPa through for example the introduction of ammonia.

The present invention provides a method for the conversion of highly purified solid melamine from melamine melt obtained from a melamine reactor, the method comprising the combination of steps of:

(a) transferring the melamine melt to a first cooling vessel, said cooling vessel having a certain pressure, preferably higher than it 5 MPa; and (b) cooling the melamine melt to a temperature just above the melting point of melamine, preferably to between 1° C. to 30° C. and more preferably to between 1° C. to 10°C. above the melting point of melamine.

(c) transferring the melamine melt to a second cooling vessel in order to convert the liquid melamine to a solid product, wherein in the second cooling vessel the melamine is further cooled using cold ammonia, preferably liquid ammonia to produce a solid pure melamine product.

DETAILED DESCRIPTION OF THE INVENTION

Applicant has discovered a method in which the purity of the melamine can be increased substantially over conventional processes for producing solid melamine from urea.

The method of the invention is capable of being practised at a plant suitable for the preparation of melamine from urea. A plant suitable for the preparation of melamine can comprise a scrubber unit, a melamine reactor integrally combined with a gas/liquid separator or optionally connected to a distinct gas/liquid separator, a first cooling vessel and a second cooling vessel. The gas/liquid separator may be integrated in the first cooling vessel.

Each of the vessels used in the process are capable of containing pressurized fluids. The transfer of materials between vessels can be by gravity force or, if desired or necessary, as augmented by mechanical pumping devices. A plant suitable for being adapted or retrofitted to permit practice of the present invention is described in U.S. Pat. No. 4,565,867, the complete disclosure of which is incorporated herein by reference.

The scrubber unit has a vessel having at least one access for urea melt input, at least one access for off-gases input, at least one outlet for urea melt discharge, and at least one outlet for $CO_2$, $NH_3$ gases discharge. The scrubber unit may be provided with a jacket so as to provide extra cooling or heating in the scrubber unit. The scrubber unit may also be provided with internal bodies or baffles.

The melamine reactor has a vessel having at least one access for a mixture comprising urea melt with liquid melamine input, optionally one access for ammonia, at least one outlet for the reaction product. This outlet may be an integral gas/liquid separator, a distinct gas/liquid separator, or an integrated gas/liquid separator and first cooling vessel. The integral gas/liquid separator or optionally, the distinct gas/liquid separator, will comprise a vessel having at least one access from the melamine reactor and at least one outlet to the scrubber unit.

The first cooling vessel has at least one access for a mixture including melamine melt, at least one access from a pump providing a cooling fluid, for example liquid ammonia or the like or one heat exchanger, and at least one outlet to the second cooling vessel. The gas/liquid separator and the first cooling vessel may be integrated into one vessel having at least one access from the melamine reactor, one access for a cooling fluid (or one heat exchanger), one outlet to a scrubber unit and one outlet to the second cooling vessel.

The second cooling vessel has at least one access for a mixture comprising liquid melamine from the first cooling vessel, at least one inlet for cold ammonia, at least one outlet excess ammonia, and at least one outlet for the solid melamine product.

The reaction of the invention which provides highly purified solid melamine from urea also produces byproducts of $NH_3$ and $CO_2$. The reaction proceeds according to the following reaction equation:

$$6\ CO(NH_2)_2 \rightarrow C_3N_6H_6 + 6NH_3 + 3CO_2$$

In a first embodiment of the invention, the first step in the production of melamine is to pump urea melt from a urea plant into a scrubber unit. The urea melt is provided to the scrubber unit at a pressure of 5 MPa to 25 MPa, preferably 8 MPa to 20 MPa, and at a temperature above the melting point of urea. In the scrubber unit the urea melt comes into contact with the off-gases $CO_2$, $NH_3$, and melamine vapour which are produced in the melamine reactor as a result of heating the melamine and ammonia mixture. The off-gases are transferred from the melamine reactor combined with a gas/liquid separator or from a distinct gas/liquid separator installed downstream of the reactor. In the case of a separate gas/liquid separator, the pressure and temperature are virtually the same as the temperature and pressure in the melamine reactor. The urea melt washes the melamine vapour out of the off-gas and carries this liquid melamine back to the reactor. In the scrubbing process the off-gases are cooled from the higher temperature of the melamine reactor, for example, from the range of 350° C. to 425° C. in the melamine reactor, to a range of 170° C. to 240° C. in the scrubber unit, the urea melt being heated to a temperature of 170°C. to 240°C. The off-gases are removed from the top of the scrubber unit and for instance returned to a urea plant for use as a starting material for the production of urea.

The urea melt is withdrawn from the scrubber unit together with the washed-out liquid melamine and transferred, for instance via a high-pressure pump, to the melamine reactor, which has a pressure of 5 MPa to 20 MPa, and preferably of 8 MPa to 20 MPa. Use can also be made of gravity for transferring the urea melt to the melamine reactor by placing the scrubber unit above the reactor.

In the melamine reactor the molten urea is heated to a temperature of 325° C. to 450° C., preferably of 350° C. to about 425° C. under which conditions the urea melt is capable of being converted into liquid melamine, $CO_2$ and $NH_3$. An additional amount of ammonia, for instance, as a liquid or hot vapour, can be metered to the reactor. The ammonia supplied can serve to prevent the formation of melamine condensation products such as melam, melem and melon, as well as promote mixing in the reactor. The amount of ammonia fed to the melamine reactor is 0 mol to 10 mol per mol urea; preferably, 0 mol to 5 mol ammonia is used, and in particular 0 mol to 2 mol ammonia per mol urea.

The $CO_2$ and $NH_3$ which are formed in the reaction, as well as the extra ammonia supplied, collect in the gas/liquid separator and contain some melamine vapour. The gas may be collected in the top of the melamine reactor; but also a distinct gas/liquid separator downstream of the reactor, optionally integrated in the first cooling vessel can be provided. The gas/liquid separator serves to separate the off-gases from the liquid melamine.

The resulting off-gases are sent to the scrubber unit for recovery of melamine and for preheating of the urea melt. The off-gases leaving the reactor and being supplied to the scrubber unit are still very near the reaction temperature of the melamine reactor and can act to heat the urea melt in the scrubber unit.

The liquid melamine is withdrawn from the gas/liquid separator and transferred to a first cooling vessel. The liquid melamine may generally contain ammonia and, but that is not preferred carbondioxide. The amount of ammonia dissolved in the melamine melt is dependent on the ammonia pressure.

In the first cooling vessel the liquid melamine melt is cooled to a temperature just above the melting point of melamine, preferably between 1° C. and 30° C. above the melting point of melamine and more preferably between 1° C. and 10° C. The temperature of the liquid melamine may be lowered by a heat exchanger or by introducing ammonia for example with a temperature of 300–370° C. In a suitable embodiment of the invention the melamine melt is cooled to a temperature above 350° C. The residence time of the liquid melamine in the cooling vessel is between two minutes and ten hours, and preferably between 10 minutes and five hours. The pressure in the first cooling vessel is preferably >5 MPa and more preferably between 8 MPa and 25 MPa. This pressure preferably being maintained through introduction of ammonia.

The resulting mixture comprising liquid melamine and ammonia is then transferred to a second cooling vessel. The pressure in the second cooling vessel may be the same pressure as the first cooling vessel. However, generally, the pressure is lower than the pressure in the first cooling vessel. The mixture comprising liquid melamine and ammonia is further cooled in the second cooling vessel by the introduction of cold ammonia or by expansion together with the introduction of cold ammonia. Thereby a highly pure powder melamine product is produced.

During the further cooling in the second cooling vessel using ammonia, the melamine melt is cooled at least 10° C., preferably at least 50° C. and more preferably at least 100° C. Additional cooling may be obtained by expanding partly or as a whole the mixture of melamine melt and ammonia.

In the second cooling vessel the composition consisting of solid melamine and ammonia is kept in contact with each other for a period of time in the range of about one minute to about five hours, preferably 5 minutes to about 3 hours, after which the mixture is expanded (if necessary) to atmospheric pressure. The pure solid melamine is recovered from the second cooling vessel and the ammonia is recirculated and reintroduced into the process.

In an alternative embodiment of the invention, cooling of the melamine mixture in the first cooling vessel is effected by raising the pressure in the first cooling vessel, after which the liquid melamine and ammonia mixture is transferred to the second cooling vessel. Preferably the cooling in the first vessel of the melamine melt is done by gradually raising the pressure in the vessel with at least 2 MPa. Preferably the pressure in the vessel is raised to a level above 10 MPa, more preferably above 20 MPa, more in particular above 50 MPa through for example the introduction of ammonia. In the second cooling vessel, the mixture is further cooled to produce solid melamine. Cooling is preferably effected by use of ammonia.

Optionally, further cooling can be augmented by expansion of the cooled mixture and/or by cooling using cold gas in an expansion vessel. The temperature and pressure in the expansion vessel prior to expansion are preferably approximately the same as the temperature and pressure in the second cooling vessel. The ammonia released as a result of the expansion step is recirculated and reintroduced into the process.

This method for the preparation of very high purity melamine has been described in patent application number Netherlands 1003709 on the date of Jul. 30, 1996, the complete disclosure of which is herein incorporated by reference.

The following non-limiting examples further describe the present invention.

EXAMPLES

Examples 1–9

Melamine was prepared from urea in a reactor (R) at a temperature of $T_R$° C. and a pressure of $P_R$ MPa. After separation of the gas phase by injection of pure ammonia, the mixture of liquid melamine and ammonia was rapidly cooled and thereafter held at a temperature in a first cooling step (C1) of $T_{C1}$° C. and a pressure of $P_{C1}$ MPa during a residence time of $t_{C1}$. The melamine was then rapidly quenched by cooling and expansion to atmosferic pressure.

The content of melamine, melam and melem in the resulting melamine powder was determined by HPLC (high performance liquid chromatography). Use was made of an anionic-exchanger (Hamilton® PRP-X100, 250 mm×4.1 mm I.D. (internal diameter)). The eluent is 0.002 M borax and 0.005 M NaCl, adjusted to pH=10.0 with 1 M NaOH.

The detection was performed with a UV-absorption spectrofotometer at 230 nm. Calibration was done with reference samples for melamine, melam and melem. For conditions and results: see table 1.

Example 10

Example 10 was performed in a way as example 3 with the exception that the melamine was rapidly quenched at an ammonia pressure of 3.0 MPa. HPLC analysis showed a melamine content of 99.2 wt. %.

Example 11

In a way as described in example 10, example 11 was performed with the exception that the melamine was rapidly quenched at an ammpnia pressure of 8 MPa. HPLC analyses showed:

melamine content 99.6 wt. %
25 melam content 0.3 wt. %
melem content <0.1 wt. %

Comparative Experiments A, B and C

Comparative experiments were performed in a way as described in Examples 1–9 with the exception that $T_R$ was equal to $T_{C1}$ and $P_R$ was equal to $P_{C1}$. For conditions and results: see table 1.

TABLE 1

| Example | $T_R$ °C. | $P_R$ MPa | $T_{C1}$ °C. | $P_{C1}$ MPa | $t_{C1}$ min | Melamine wt. % | Melam wt. % | Melem wt. % |
|---|---|---|---|---|---|---|---|---|
| 1 | 410 | 15 | 360 | 15 | 20 | 98.5 | 1.2 | 0.08 |
| 2 | 405 | 15 | 335 | 15 | 60 | 99 | 0.8 | 0.04 |
| 3 | 400 | 15 | 360 | 15 | 90 | 98.6 | 1.1 | 0.1 |
| 4 | 390 | 8.5 | 350 | 15 | 60 | 98.6 | 1.1 | 0.06 |
| 5 | 390 | 8.5 | 335 | 20 | 105 | 99.4 | 0.5 | 0.02 |
| 6 | 405 | 14 | 325 | 20 | 90 | 99.4 | 0.4 | 0.01 |
| 7 | 400 | 14 | 320 | 25 | 120 | 99.6 | 0.3 | <0.01 |
| 8 | 410 | 15 | 270 | 50 | 90 | 99.8 | <0.1 | <0.01 |
| 9 | 410 | 15 | 270 | 80 | 90 | 99.9 | <0.1 | <0.01 |
| A | 405 | 15 | 405 | 15 | 90 | 97 | 2.4 | 0.3 |
| B | 400 | 15 | 400 | 15 | 10 | 97 | 2.6 | 0.3 |
| C | 385 | 8.5 | 385 | 8.5 | 40 | 94 | 3.8 | 0.6 |

What is claimed is:

1. A method of preparing highly pure solid melamine from urea melt, the method comprising the combination of steps of:
   (a) introducing urea melt and off-gases comprising $CO_2$, $NH_3$, and melamine vapour into a scrubber unit at a pressure of 5 MPa to 25 MPa and a temperature of 170° C. to 240° C. whereby said melamine vapour is dissolved in said urea melt;
   (b) transferring said urea melt comprising said melamine as a urea melt mixture from said scrubber unit to a melamine reactor and heating said urea melt mixture in said melamine reactor to a temperature of 325° C. to 450° C. and a pressure of 5 MPa to 25 MPa sufficient to convert said urea melt mixture to a melamine melt and off-gases;
   (c1) separating said off-gases from said melamine melt and
   (c2) transferring said melamine melt to a first cooling vessel, the pressure in the cooling vessel being higher than 5 MPa and cooling the melamine melt to a temperature between 1° C. and 30° C. above the melting point of melamine;
   (d) transferring said liquid melamine to a second cooling vessel in order to convert the liquid melamine to a solid product, wherein in the second cooling vessel melamine is further cooled using cold ammonia, to produce a pure solid melamine.

2. The method according to claim 1 wherein the melamine melt is cooled to a temperature between 1° C. and 10° C. above the melting point of melamine.

3. The method according to anyone of claims 1–2, wherein steps (c1) and (c2) are taken place in one vessel.

4. The method according to any one of claims 1–3 wherein herein said highly pure solid melamine is obtained by cooling and expansion.

5. The method according to any one of claims 1–4, wherein said melamine melt in said second cooling vessel is cooled at least 10° C.

6. The method according to claim 5 wherein said melamine melt in said second cooling vessel is cooled at least 50° C.

7. The method according to any one of claims 1–6 wherein the pressure of said melamine melt in the first cooling vessel is increased with respect to the pressure in the reactor.

8. The method of claim 7 wherein said pressure in said first cooling vessel is attained by the gradual introduction of ammonia.

9. The method of any one of claims 7–8 wherein the pressure of said melamine melt in said first cooling vessel is gradually raised with at least 2 MPa.

10. A method according to any one of claims 1–9, wherein melamine is obtained having a purity measured with HPLC of 98.5–99.95%.

11. A method according to any one of claims 1–10, wherein melamine is obtained having a purity in HPLC of 99.5–99.95%.

12. A method of controlling the formation of deaminoniation byproducts melam and melem in highly pure solid melamine from urea melt, the method comprising the steps of:
   (a) introducing urea melt and off-gases comprising $CO_2$, $NH_3$, and melamine vapor into a scrubber unit, said scrubber unit being operated at a pressure of from 5 MPa to 25 MPa and a temperature of from 170° C. to 240° C., whereby said melamine vapor is dissolved in said urea melt;
   (b) transferring said urea melt comprising said melamine as a urea melt mixture from said scrubber unit to a melamine reactor and heating said urea melt mixture to a temperature of from 325° C. to 450° C. at a pressure of from 5 MPa to 25 MPa to convert said urea melt mixture to a melamine melt and off-gases;

(c) separating said off-gases from said melamine melt;

(d) cooling said melamine melt to a predetermined temperature in a first cooling vessel, the pressure in said cooling vessel being at least 5 MPa, said predetermined temperature being between 1° C. and 30° C. above the melting point of melamine at the pressure within the cooling vessel to form a cooled melamine melt;

(e) transferring said cooled melamine melt to a solidification vessel wherein said melamine melt is solidified using cold ammonia; and thereby (f) producing a solid melamine product exhibiting reduced levels of deammoniation byproducts melam and melem, wherein the level of melem in said solid melamine product is lower than the level of melam.

13. A method of controlling the formation of deammoniation byproducts melam and melem in highly pure solid melamine from urea melt according to claim 12, wherein the the steps of (c) separating said off-gases and (d) cooling said melamine melt are performed in a single vessel.

14. A method of controlling the formation of deammoniation byproducts melam and melem in highly pure solid melamine from urea melt according to claim 12 wherein the pressure in the cooling vessel is at least 2 MPa higher than the pressure in the melamine reactor.

15. A method of controlling the formation of deammoniation byproducts melam and melem in highly pure solid melamine from urea melt according to claim 12 wherein the predetermined temperature in the first cooling vessel is at least 50° C. lower than the temperature in the melamine reactor.

* * * * *